United States Patent
Crow

(10) Patent No.: US 7,736,375 B2
(45) Date of Patent: Jun. 15, 2010

(54) BALLOON CATHETER WITH CONTROLLER DEPTH INCISING BLADE

(75) Inventor: Loren M. Crow, La Mesa, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1155 days.

(21) Appl. No.: 10/998,455

(22) Filed: Nov. 29, 2004

(65) Prior Publication Data

US 2006/0116701 A1 Jun. 1, 2006

(51) Int. Cl.
*A61B 17/32* (2006.01)
(52) U.S. Cl. ...................... 606/159; 606/167
(58) Field of Classification Search ............... 606/159, 606/167, 170, 192–194, 172; 604/22, 96.01; 30/305; 7/118, 119
See application file for complete search history.

(56) References Cited

U.S. PATENT DOCUMENTS

| | | | |
|---|---|---|---|
| 4,768,508 A * | 9/1988 | Chin et al. ............... | 606/159 |
| 5,009,659 A | 4/1991 | Hamlin et al. | |
| 5,085,663 A * | 2/1992 | Tarr ........................ | 606/172 |
| 5,092,872 A | 3/1992 | Segalowitz | |
| 5,112,900 A | 5/1992 | Buddenhagen et al. | |
| 5,176,693 A | 1/1993 | Pannek, Jr. | |
| 5,196,024 A | 3/1993 | Barath | |
| 5,209,799 A | 5/1993 | Vigil | |
| 5,320,634 A | 6/1994 | Vigil et al. | |
| 5,336,234 A | 8/1994 | Vigil et al. | |
| 5,348,538 A | 9/1994 | Wang et al. | |
| 5,403,340 A | 4/1995 | Wang et al. | |
| 5,447,497 A | 9/1995 | Sogard et al. | |
| 5,549,552 A | 8/1996 | Peters et al. | |
| 5,550,180 A | 8/1996 | Elsik et al. | |
| 5,556,383 A | 9/1996 | Wang et al. | |
| 5,556,405 A | 9/1996 | Lary | |
| 5,556,408 A | 9/1996 | Farhat | |
| 5,616,149 A | 4/1997 | Barath | |
| 5,697,944 A | 12/1997 | Lary | |
| 5,713,913 A | 2/1998 | Lary et al. | |
| 5,728,123 A * | 3/1998 | Lemelson et al. ......... | 604/22 |
| 5,792,158 A | 8/1998 | Lary | |
| 5,797,935 A | 8/1998 | Barath | |
| 5,830,182 A | 11/1998 | Wang et al. | |
| 5,843,116 A * | 12/1998 | Crocker et al. ........... | 606/192 |
| 5,951,941 A | 9/1999 | Wang et al. | |
| 6,096,054 A | 8/2000 | Wyzgala et al. | |
| 6,146,356 A | 11/2000 | Wang et al. | |

(Continued)

*Primary Examiner*—Anhtuan T Nguyen
*Assistant Examiner*—Ryan J Severson
(74) *Attorney, Agent, or Firm*—Crompton, Seager & Tufte, LLC.

(57) ABSTRACT

A device for incising tissue to a pre-selected incision depth within a body conduit of a patient includes an elongated balloon catheter and at least one elongated straight blade that is mounted on the balloon. To control the incision depth, each blade has a blunt section formed with a non-incising surface and a cutting edge positioned distally to the blunt section. A proximal portion of the blade is attached to a proximal balloon section, and in operation, the balloon/blade combination is advanced into the body conduit and positioned distal to the target tissue/stenosis. The balloon is then inflated. With this inflation, the blade is inclined relative to the axis of the catheter with an increasing distance between the blade and the axis in a distal direction. The device is then withdrawn, proximally, to incise the tissue/stenosis.

19 Claims, 3 Drawing Sheets

U.S. PATENT DOCUMENTS

| | | |
|---|---|---|
| 6,171,278 B1 | 1/2001 | Wang et al. |
| 6,258,108 B1 | 7/2001 | Lary |
| 6,306,151 B1 | 10/2001 | Lary |
| 6,328,925 B1 | 12/2001 | Wang et al. |
| 6,406,457 B1 | 6/2002 | Wang et al. |
| 6,746,463 B1 | 6/2004 | Schwartz |

\* cited by examiner

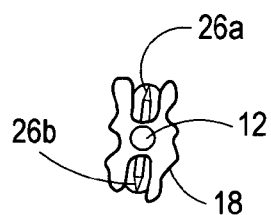
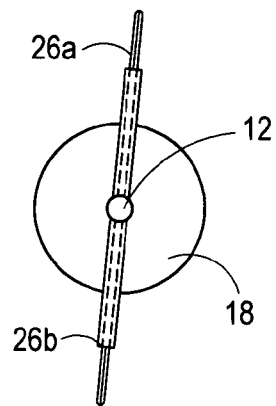
Fig. 3A
Fig. 3B
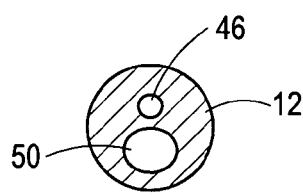
Fig. 4
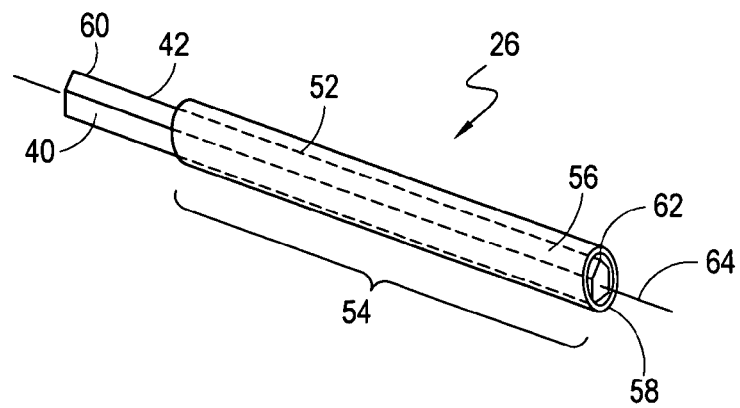
Fig. 5

BALLOON CATHETER WITH CONTROLLER DEPTH INCISING BLADE

FIELD OF THE INVENTION

The present invention pertains generally to subcutaneous, interventional medical devices. More particularly, the present invention pertains to catheters that can be used to incise target tissue in the vasculature of a patient at a controlled cutting depth. The present invention is particularly, but not exclusively, useful for incising an aortic valve stenosis with a catheter having a blade configured to incise at a pre-selected cutting depth.

BACKGROUND OF THE INVENTION

The creation of superficial incisions within a body conduit can be used for several purposes. For example, a properly placed incision can be used to facilitate the dilation of the conduit's lumen when the conduit is stenosed or otherwise blocked. Applications where the creation of an incision is beneficial can include, but are not limited to, the dilation of vessels and valves in the vasculature. Other conduits where incisions can be used for dilation and other purposes include the esophagus, urethra and portions of the airway system. For some (if not all) of these applications, it is important to control the depth of the incision. If the incision is too shallow, the incision will be ineffective in promoting dilation of the conduit lumen. On the other hand, if the incision is too deep, the incision can cause damage to underlying tissue. This underlying tissue can include vital organs, nerves and nerve endings, and other delicate anatomical structures, the damage of which may be irreparable.

One exemplary application which warrants further discussion is the incision and dilation of the aortic valve as a treatment for Aortic Valve Stenosis (AS). Functionally, the aortic valve controls the flow of oxygen-rich blood from the left ventricle into the aorta. Anatomically, the aortic valve consists of three semilunar cusps (i.e. right, left and posterior cusps) that are attached around the circumference of an opening that is located between the aorta and left ventricle. During each heart cycle, the cusps (also called flaps or leaflets) fold back against the inside wall of the aorta as the left ventricle contracts, effectively opening the aortic valve to allow blood to be pumped through the aorta and into the arteries in the vasculature of the body. Between contractions of the left ventricle, however, the cusps extend into the passageway between the left ventricle and aorta to close the aortic valve and form a tight seal that prevents blood from leaking back into the left ventricle from the aorta.

For any of several reasons (e.g. aging, or birth defects), it can happen that the aortic valve is somehow damaged and may become stenosed. When this happens, the aortic valve does not open to its normal extent and the flow of blood from the heart into the aorta is constricted. This leads to an undesirable heart condition that is commonly known as aortic valve stenosis (AS). If left untreated, AS can worsen and lead to a number of complications including endocarditis, arrhythmia and in some cases heart failure.

Heretofore, the conventional methods used to treat AS have typically involved either an aortic valve replacement or a procedure commonly known as percutaneous balloon valvuloplasty. In the case of a valve replacement, an extensive surgical procedure is generally required in which the aortic valve is replaced either by a mechanical or a porcine valve. On the other hand, being a percutaneous procedure, balloon valvuloplasty is somewhat less involved than a valve replacement procedure. Nevertheless, for many reasons including a high recurrence rate, and despite its initial acceptance, balloon valvuloplasty is now used infrequently and only palliatively or as a bridge to a subsequent valve replacement.

More recently, efficacious treatments for aortic valve stenosis have been developed which entail incising and dilating the stenosed aortic valve. For example, a device and method for treating AS is disclosed in co-pending, co-owned U.S. patent application Ser. No. 10/353,827, filed by Leonard Schwartz (Schwartz '827) on Jan. 27, 2003, for an invention titled "A Device for Percutaneous Cutting and Dilating a Stenosis of the Aortic Valve", and which is hereby incorporated by reference in its entirety.

As indicated above, in some applications, it is important to control the depth of the incision. In this regard, the present invention is directed to a percutaneous device and method for making incisions in a body conduit having a controlled, pre-selected incision depth. Preferably, the invention provides a cutting device for treating aortic valve stenosis by making controlled depth incisions in the aortic valve to thereby establish a more normal flow of blood from the left ventricle of the heart into the aorta.

SUMMARY OF THE INVENTION

In accordance with the present invention, a device for incising to a pre-selected incision depth within a body conduit of a patient includes a catheter having an elongated balloon mounted near its proximal end. As intended for the present invention, the balloon can be reconfigured on the catheter between an inflated configuration and a deflated configuration. Structurally, the balloon defines an axis and, in its inflated configuration, it has at least three identifiable sections that are located between its proximal end and its distal end. These sections are: a substantially conical-shaped proximal section having a taper with an increasing radius in the distal direction; a substantially conical-shaped distal section having a taper with a decreasing radius in the distal direction; and a substantially cylindrical-shaped intermediate section that is located between the proximal section and the distal section.

One or more substantially straight, elongated blades are attached to the balloon. Each blade defines a blade axis and extends from a distal blade end to a proximal blade end. In a particular embodiment of the cutting device, a proximal portion of each blade is attached to the proximal section of the balloon. On the other hand, for this embodiment, the distal end of each blade is detached from the balloon to allow the blade to incline relative to the balloon axis when the balloon is inflated.

To control the incision depth, each blade has a blunt section formed with a non-incising surface that extends completely around the blade axis. In more detail, the blunt section is positioned proximally from the distal blade end to interpose a cutting edge between the non-incising surface and the distal blade end. The non-incising surface can be attached to a portion of the blade having the cutting edge or integrally formed thereon. In one embodiment of the present invention, the non-incising surface includes a rounded surface portion. For example, a blade can be formed initially having a sharp blade edge that extends from the distal blade end to the proximal blade end and thereafter a proximal portion of the sharp blade edge can be rounded to create the non-incising surface.

In another embodiment of the blade, a protective sheath can be positioned to overlay a proximal portion of the sharp blade edge. In one implementation, a plastic, tubular shaped protective sheath is used to cover a proximal portion of the sharp blade edge. In yet another embodiment of the blade, a spherical shaped member having a substantially spherical non-incising surface is formed at a location on the blade proximal to the distal blade end. In a particular implementation of this embodiment, the spherical member is sized having a diameter, 2 r, that is larger than the blades maximum dimension, d, normal to the blade axis (d<2 r). For all of these blade embodiments, a blunt section having a non-incising surface is created to control (i.e. limit) the incision depth.

In the operation of the present invention, the balloon (in its deflated configuration) is advanced into the body conduit (e.g. vasculature) of the patient. Specifically, for the exemplary case where the invention is used for the treatment of AS, the balloon is routed through the aorta and positioned inside the left ventricle of the heart. This then places the balloon distal to the aortic valve. Once the balloon is in the left ventricle it is then inflated.

In its inflated configuration, the balloon inclines each blade relative to the axis of the balloon. Specifically, this inclination is characterized by an increasing distance between the blade and the axis of the balloon, in a distal direction along the axis. In cooperation with the balloon, each blade is inclined relative to the balloon's axis at an angle ($\alpha$) that is established by the taper of the balloon's proximal section, when the balloon is inflated. Thus, the angle of the blade can be any angle suitable for an angioplasty balloon. Preferably, this angle ($\alpha$) is in a range between approximately zero degrees and approximately forty-five degrees ($0°<\alpha<45°$). As a consequence of this cooperation of structure, when the balloon is in its inflated configuration, the cutting edges of the blade(s) are presented for cutting (incising) the aortic valve. More specifically, the distal ends of the respective blade(s) are projected radially outward from the axis through a distance that extends beyond the radius of the cylindrical-shaped intermediate section.

An incising action on the aortic valve is accomplished as the inflated balloon is withdrawn through the aortic valve in a proximal direction. Specifically, the cutting edge penetrates the tissue or lesion to be incised until the non-incising surface contacts the tissue/lesion. At this point, the incision depth is set and further withdrawal of the inflated balloon results in an incision having a somewhat constant, controlled incision depth. After the inflated balloon has been withdrawn through the aortic valve, and the valve has been incised, the balloon is deflated, retracting each blade into its original, non-inclined orientation. The deflated balloon and retracted blade(s) are then removed from the vasculature to complete the procedure.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which:

FIG. 3A is an end view of the balloon of the device of the present invention as seen along the line 3A-3A in FIG. 2A;

FIG. 3B is an end view of the balloon of the device of the present invention as seen along the line 3B-3B in FIG. 2B;

FIG. 4 is a cross sectional view of the catheter as seen along the line 4-4 in FIG. 1;

FIG. 5 is an enlarged perspective view of the blade shown in FIG. 1;

DESCRIPTION OF THE PREFERRED EMBODIMENTS

Figure 1:
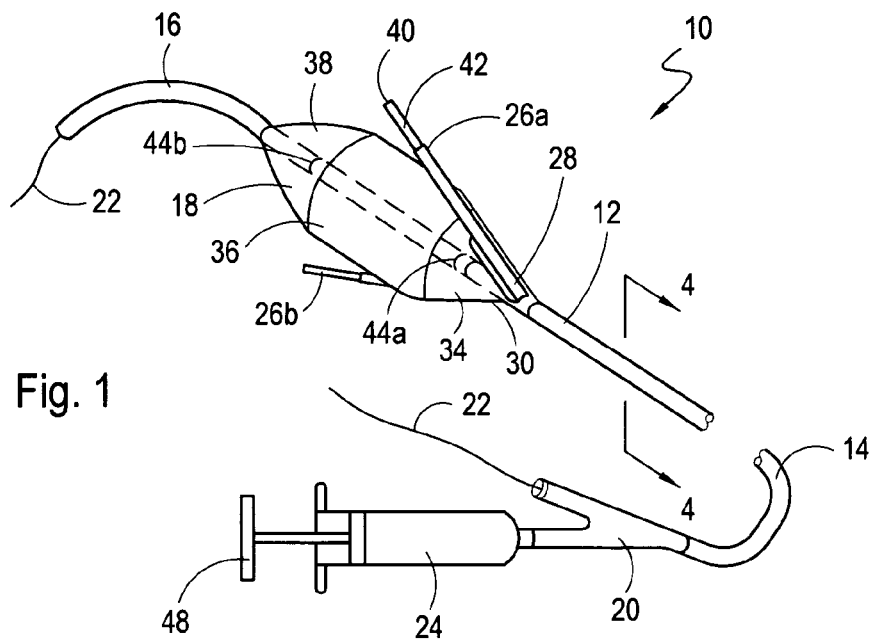
FIG. 1 is a perspective view of the incising device of the present invention.

Referring initially to FIG. 1, a system for incising tissue in accordance with the present invention is shown and generally designated 10. As shown, the system 10 includes a catheter 12 which has a proximal end 14 and a distal end 16. System 10 also has an inflatable, elongated balloon 18 that is mounted on the catheter 12 near its distal end 16. Further, it is seen that a y-site 20 is attached to the proximal end 14 of the catheter 12. Specifically, the y-site 20 allows the catheter 12 to be operationally engaged with a guidewire 22 for the purpose of advancing the catheter 12 over the guidewire 22 after the guidewire 22 has been pre-positioned in a body conduit, such as the vasculature, of a patient (not shown). FIG. 1 also shows that an inflation/deflation device 24 can be connected to the y-site 20 for fluid communication with the balloon 18.

For the catheter 12, the inflatable balloon 18 can be made of a compliant, semi-compliant or non-compliant material. Specifically, any suitable thermoplastic or thermosetting material may be used in accordance herewith including both elastomeric and non-elastomeric materials. Thermoplastic materials find particular utility herein. Examples of non-elastomeric materials include, but are not limited to, polyolefins including polyethylene and polypropylene, polyesters, polyethers, polyamides, polyurethanes, polyimides, and so forth, as well as copolymers and terpolymers thereof. As used herein, the term "copolymer" shall hereinafter be used to refer to any polymer formed from two or more monomers.

Examples of suitable elastomeric materials include, but are not limited to, elastomeric block copolymers including the styrenic block copolymers such as styrene-ethylene/butylene-styrene (SEBS) block copolymers disclosed in U.S. Pat. No. 5,112,900 which is incorporated by reference herein in its entirety. Other suitable block copolymer elastomers include, but are not limited to, styrene-isoprene-styrene (SIS), styrene-butadiene-styrene (SBS), styrene-isobutylene-styrene (SIBS) and so forth. Block copolymer elastomers are also described in commonly assigned U.S. Pat. Nos. 6,406,457, 6,171,278, 6,146,356, 5,951,941, 5,830,182 and 5,556,383, each of which is incorporated by reference herein in its entirety.

Elastomeric polyesters and copolyesters may be employed herein. Examples of elastomeric copolyesters include, but are not limited to, poly(ester-block-ether) elastomers, poly(ester-block-ester) elastomers and so forth. Poly(ester-block-ether) elastomers are available under the trade name of HYTREL® from DuPont de Nemours & Co. and consist of hard segments of polybutylene terephthalate and soft segments based on long chain polyether glycols. These polymers are also available from DSM Engineering Plastics under the trade name of ARNITEL®.

Non-elastomeric polyesters and copolymers thereof may be employed, such as the polyalkylene naphthalates, including polyethylene terephthalate and polybutylene terephthalate, for example. Polyamides including nylon, and copolymers thereof, such as poly (ether-block-amides) available under the trade name of PEBAX® from Atofina Chemicals in Philadelphia, Pa., are suitable for use herein. Suitable balloon materials are described in commonly assigned U.S. Pat. Nos. 5,549,552, 5,447,497, 5,348,538, 5,550,180, 5,403,340 and 6,328,925, each of which is incorporated by reference herein in its entirety. The above lists are intended for illustrative purposes only, and shall not be construed as a limitation on the scope of the present invention.

Still referring to FIG. 1, it will be seen that the system 10 of the present invention includes a plurality of substantially straight blades 26, of which the blades 26a and 26b are only exemplary. The system 10 may include only one such blade 26, or it may include more than one blade 26 (e.g. two, three or more). With this in mind, and using the blade 26a as a specific example for purposes of disclosure, it will be seen that the proximal end 28 of the blade 26a is positioned adjacent, or near, the proximal end 30 of the balloon 18. Further, it is to be appreciated that the blade 26a is oriented on the balloon 18 so that it is coplanar with the longitudinal axis 32 of the balloon 18 (see FIG. 2A). Also, it is to be appreciated by cross-referencing FIG. 1 with FIG. 2B, that the blade 26a is attached to a proximal section of the balloon 18. For purposes of the present invention, the blades 26 can be attached to the balloon 18 by any means well known in the pertinent art, such as by bonding.

Figure 2A:
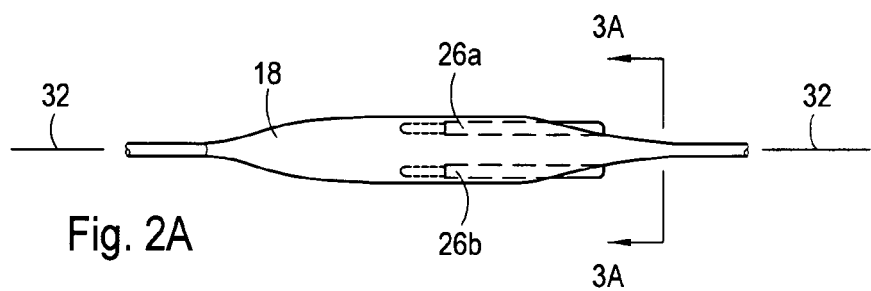
FIG. 2A is a side view of the balloon of the device of the present invention when the balloon is in its deflated configuration.
Figure 2B:
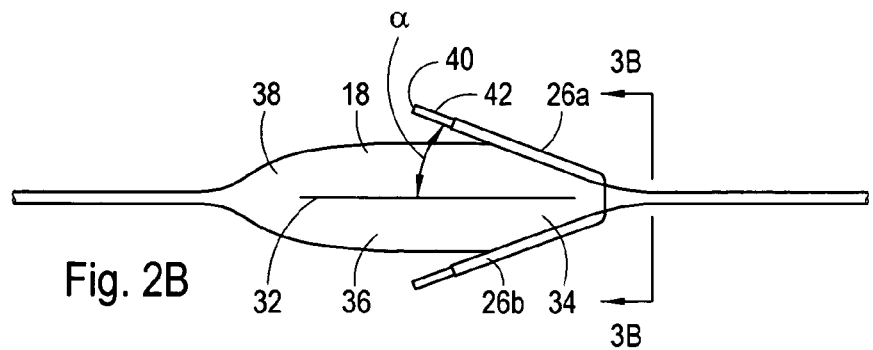
FIG. 2B is a side view of the balloon of the device of the present invention when the balloon is in its inflated configuration.

The structure for balloon 18 will be best understood by referencing both FIGS. 1 and 2B. As shown, the balloon 18, when inflated, generally defines three sections. These are: a proximal section 34; an intermediate section 36; and a distal section 38. More specifically, when the balloon 18 is inflated, the proximal section 34 is generally conical-shaped and has a taper with an increasing radius in the distal direction. On the other hand, the intermediate section 36 is substantially cylindrical-shaped and has a generally constant radius. Also, there is a conical-shape for the distal section 38. This time, however, the taper for the distal section 38 has a decreasing radius in the distal direction. Preferably, the blade 26a is longer than the proximal section 34 and is attached to only the proximal section 34 of the balloon 18. Consequently, the distal end 40 of the blade 26a is not engaged with the balloon 18. As perhaps best seen in FIG. 2B, this cooperation of structure allows the distal end 40 of the blade 26a, to extend radially outward from the axis 32 to a greater distance than the radius of the cylindrical-shaped intermediate section 36. Stated differently, with the balloon 18 in its inflated configuration, the blades 26 are inclined at an angle ($\alpha$) relative to the axis 32. Preferably, the angle ($\alpha$) is in a range between 0° and 45°.

FIG. 1 also shows that the system 10 of the present invention can include radiopaque markers 44a and 44b to assist the operator in positioning the balloon 18 in the vasculature of the patient. Identification of the balloon 18 at a location in the vasculature can be further facilitated by using a contrast medium to inflate the balloon 18. Other mechanisms, well known in the pertinent art, can be incorporated in the system 10 and used for these purposes.

As envisioned for the present invention, the balloon 18 of the present invention can be reconfigured between a deflated configuration (FIGS. 2A and 3A) and an inflated configuration (FIGS. 2B and 3B). The actual inflation and deflation of the balloon 18 is accomplished by manipulating the inflation device 24 (See FIG. 1). Specifically, for this purpose, the inflation/deflation device 24 is connected at the y-site 20 in fluid communication with an inflation lumen 46 (see FIG. 4). A manipulation of the plunger 48 (see FIG. 1) can then cause the balloon 18 to selectively inflate or deflate. FIG. 4 also shows that the catheter 12 is formed with a guidewire lumen 50 for receiving the guidewire 22 therethrough.

As best seen in FIG. 5, each blade 26 has a sharp blade edge 52 and includes a blunt section 54 having a non-incising surface 56 to control incision depth. For the blade 26 shown in FIGS. 1-5, the blunt section 54 consists of a tubular shaped, protective sheath 58 that is positioned to overlay a distal portion of sharp blade edge 52. More specifically, for this embodiment, the sharp blade edge 52 extends from a distal edge end 60 to a proximal edge end 62 and the protective sheath 58 overlays and covers a proximal portion of the sharp blade edge 52. It can further be seen that the elongated blade 26 defines a blade axis 64 and the non-incising surface 56 of the blunt section 54 extends completely around the blade axis 64. Moreover, the blunt section 54 is positioned proximally from the distal end 40 of the blade 26 to project an exposed cutting edge 42 distally from the blunt section 54. For this embodiment of the blade 26, the blunt section 54 can be, but is not limited to, a sheath 58 that encapsulates a proximal portion of the blade 26 (as shown) or a coating (not shown) that is applied directly to the sharp blade edge 52. In a particular embodiment, the protective sheath 58 can be made of a polymeric material (e.g. plastic) and bonded to a proximal portion of the blade 26.

Figure 6:
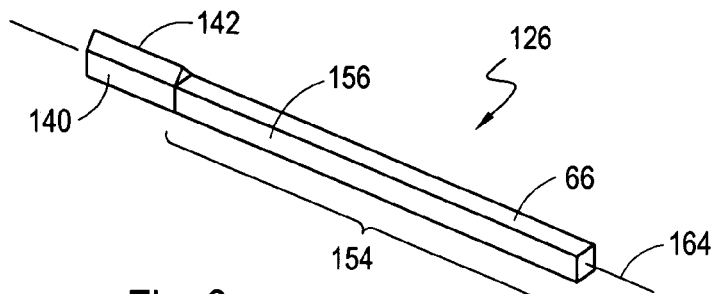
FIG. 6 is an enlarged perspective view of another embodiment of a blade for use in the present invention having a blunt section that includes a rounded non-incising surface.

FIG. 6 shows another embodiment of a blade (designated 126) having a blunt section 154 for use in the system 10 shown in FIG. 1 to control incision depth. As shown in FIG. 6, the blunt section 154 is positioned proximally from the distal end 140 of the blade 126 to project an exposed cutting edge 142 distally from the blunt section 154. FIG. 6 also shows that the blunt section 154 establishes a non-incising surface 156, which includes a rounded surface portion 66, and extends completely around the blade axis 164. With this cooperation of structure, the blade 126 can be used in the system 10 to effect a controlled depth incision. In an exemplary manufacturing method, the blade 126 can be prepared by initially forming a blade blank (not shown) having a sharp blade edge that extends the entire length of the blade blank. Next, a proximal portion of the sharp blade edge can be rounded (i.e. dulled) to create the non-incising surface 156.

Figure 7:
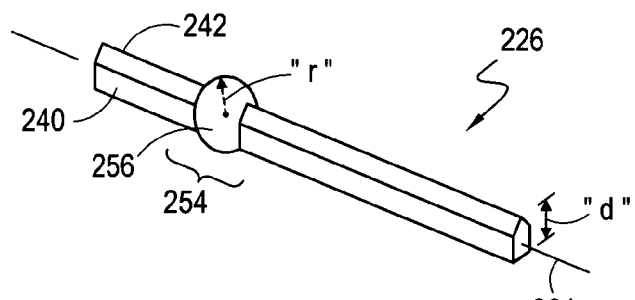
FIG. 7 is an enlarged perspective view of another embodiment of a blade for use in the present invention having a blunt section with a substantially spherical, non-incising surface.

Referring now to FIG. 7, another embodiment of a blade (designated 226) is shown having a blunt section 254 for use in the system 10 shown in FIG. 1 to control incision depth. As shown in FIG. 7, the blunt section 254 is positioned proximally from the distal end 240 of the blade 226 to project an exposed cutting edge 242 distally from the blunt section 254. FIG. 7 also shows that the blunt section 254 establishes a non-incising surface 256 which is substantially spherical, and extends completely around the blade axis 264. For the embodiment shown in FIG. 7, the spherical, blunt section 254 is sized having a diameter, $2r$, that is larger than the maximum dimension, $d$, of the blade 226, normal to the blade axis 264 ($d<2r$). With this cooperation of structure, the blade 226 can be used in the system 10 to effect a controlled depth incision.

Figure 8:
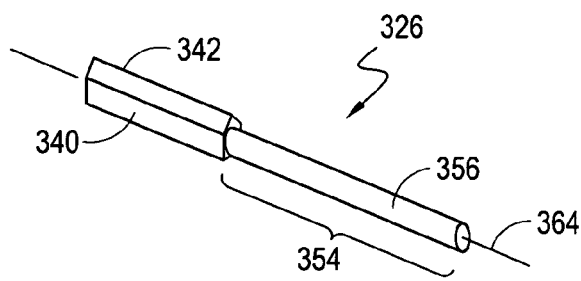
FIG. 8 is an enlarged perspective view of another embodiment of a blade for use in the present invention having a blunt section formed as a wire.

FIG. 8 shows yet another embodiment of a blade (designated 326) having a blunt section 354 for use in the system 10 shown in FIG. 1 to control incision depth. As shown in FIG. 8, the blunt section 354 is positioned proximally from the distal end 340 of the blade 326 to project an exposed cutting edge 342 distally from the blunt section 354. FIG. 8 also shows that the blunt section 354 establishes a non-incising surface 356, which is substantially cylindrical shaped, and extends completely around the blade axis 364. In a typical embodiment, the blunt section 354 is formed as a wire and then attached to the remaining portion of the blade 326 that includes the cutting edge 342. With this cooperation of structure, the blade 326 can be used in the system 10 to effect a controlled depth incision.

Figure 9:
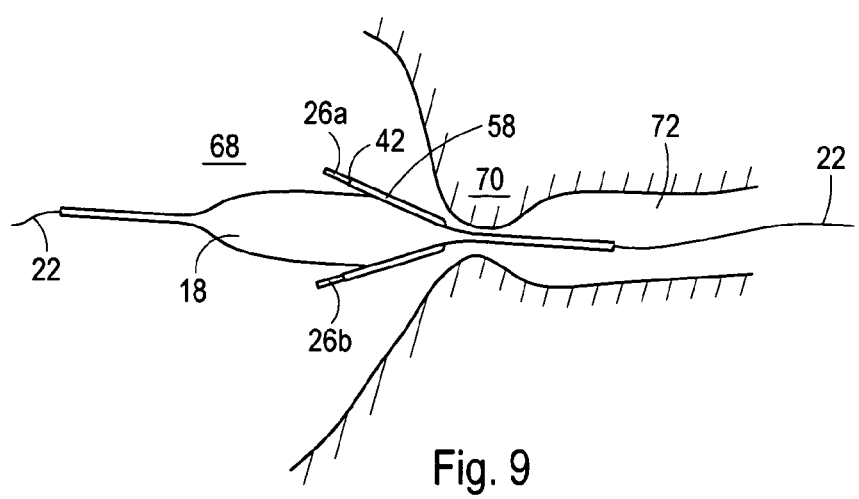
FIG. 9 is a schematic view of an inflated balloon of the present invention, positioned inside the left ventricle of a patient, ready for withdrawal in a distal direction to incise the aortic valve.

Referring now to FIG. 9, an exemplary application of the system 10 is illustrated wherein the system 10 is used to treat Aortic Valve Stenosis. Although the exemplary treatment of an aortic valve stenosis is hereinafter described, it is to be appreciated that the system 10 can be used to incise tissue (including stenosed tissue) in other areas of the body. For the procedure, a guidewire 22 is first pre-positioned in the vasculature of the patient. Next, the catheter 12, with the balloon 18 in its deflated configuration (i.e. as shown in FIGS. 2A and 3A) is then advanced over the guidewire 22. Specifically, as shown, the balloon 18 is advanced over the guidewire 22 until the balloon 18 has been positioned in the left ventricle 68 of the patient's heart. At this point, the inflation/deflation device 24 is manipulated to inflate the balloon 18 into its inflated configuration (FIGS. 1, 2B and 3B). With the cutting blades 26 radially deployed, the system 10 is then withdrawn in a proximal direction through the aortic valve 70 and into the aorta 72. During this withdrawal, the cutting edges 42 of respective blades 26 incise the aortic valve 70 to relieve any stenosis that has developed in the aortic valve 70. After incision, the balloon 18 is deflated, and the system 10 is removed from the vasculature of the patient.

While the particular Balloon Catheter With Controlled Depth Incising Blade and corresponding methods of manufacture and use as herein shown and disclosed in detail are fully capable of obtaining the objects and providing the advantages herein before stated, it is to be understood that they are merely illustrative of the presently preferred embodiments of the invention and that no limitations are intended to the details of construction or design herein shown other than as described in the appended claims.

What is claimed is:

1. A device for incising tissue to a pre-selected incision depth within a body conduit of a patient, the device comprising:
    a catheter;
    an elongated balloon defining an axis, the balloon being mounted on the catheter for reconfiguration between an inflated configuration and a deflated configuration; and
    a substantially straight elongated blade having a distal end and a proximal end and defining a blade axis, with the proximal end thereof attached to the balloon to orient the blade in a plane with the axis of the balloon and to project a sharp edge at the distal end of the blade in a radial direction from the axis of the balloon when the balloon is inflated, the blade having a blunt section positioned proximal to the sharp edge to limit the incision of tissue by the sharp edge of the blade to the pre-selected incision depth during a proximal movement of the balloon in its inflated configuration.

2. A device as recited in claim 1 further comprising a guidewire for advancing the catheter through the body conduit to position the balloon for cutting tissue at a predetermined site in the body conduit.

3. A device as recited in claim 1 wherein the balloon has a proximal end and a distal end and, in its inflated configuration, the balloon further comprises:
    a substantially conical-shaped proximal section having a taper with increasing radius in the distal direction;
    a substantially conical-shaped distal section having a taper with decreasing radius in the distal direction;
    a substantially cylindrical-shaped intermediate section located between the proximal section and the distal section; and
    wherein the blade is attached to the proximal section of the balloon with the proximal end of the blade adjacent the proximal end of the balloon.

4. A device as recited in claim 1 wherein the blunt section is formed with a rounded surface portion.

5. A device as recited in claim 1 wherein the blunt section comprises a protective sheath overlaying a sharp blade edge.

6. A device as recited in claim 1 wherein the blunt section is formed with a substantially spherical surface.

7. A device for incising to a pre-selected incision depth within a body conduit of a patient, the device comprising:
    a substantially straight elongated blade defining a blade axis and having a blunt section and a cutting edge section, the blunt section formed with a non-incising surface, with the blunt section positioned proximally from the cutting edge section to limit incision to the cutting edge section of the blade;
    a means for advancing the elongated blade in a distal direction along a predetermined path in the body conduit;
    a means for inclining the blade relative to the path with an increasing distance between the blade and the path in the distal direction; and
    a means for withdrawing the blade in a proximal direction along the path.

8. A device as recited in claim 7 wherein the advancing means is a catheter and the inclining means is a balloon.

9. A device as recited in claim 8 wherein the balloon has a proximal end and a distal end and, when inflated, the balloon further comprises:
    a substantially conical-shaped proximal section having a taper with increasing radius in the distal direction;
    a substantially conical-shaped distal section having a taper with decreasing radius in the distal direction; and
    a substantially cylindrical-shaped intermediate section located between the proximal section and the distal section.

10. A device as recited in claim 9 wherein the blade is attached to the proximal section of the balloon with the proximal end of the blade adjacent the proximal end of the balloon.

11. A device as recited in claim 7 wherein the blunt section is formed with a rounded surface portion.

12. A device as recited in claim 7 wherein the blunt section comprises a protective sheath overlaying a sharp blade edge.

13. A device as recited in claim 12 wherein the protective sheath is made of plastic.

14. A device as recited in claim 12 wherein the protective sheath is tubular shaped.

15. A device as recited in claim 7 wherein the blunt section is formed with a substantially spherical surface.

16. A device as recited in claim 15 wherein the blade has a maximum dimension, d, normal to the blade axis and the substantially spherical surface has a radius, r, with $d<2r$.

17. A method for incising tissue to a pre-selected incision depth at an incision location within a body conduit of a patient, the method comprising the steps of:
    providing a substantially straight elongated blade defining a blade axis and having a blunt section and a cutting edge section, the blunt section formed with a non-incising surface, with the blunt section positioned proximally from the cutting edge section to limit incision to the cutting edge section of the blade;

advancing the elongated blade in a distal direction along a predetermined path into the body conduit of a patient, to position the blade distal to the incision location;

inclining the blade relative to the path with an increasing distance between the blade and the path in the distal direction; and withdrawing the blade in a proximal direction along the path to incise at the pre-selected incision depth.

18. A method as recited in claim 17 wherein the non-incising surface comprises a rounded surface portion.

19. A method as recited in claim 17 wherein the blunt section comprises protective sheath overlaying a sharp blade edge.

* * * * *